United States Patent [19]
Brown, Sr.

[11] Patent Number: 5,571,209
[45] Date of Patent: Nov. 5, 1996

[54] POST-OPERATIVE PROTECTIVE PROSTHESIS

[75] Inventor: Robert N. Brown, Sr., Ithaca, N.Y.

[73] Assignee: Flo-Tech Orthotic & Prosthetic Systems, Inc., Ithaca, N.Y.

[21] Appl. No.: 379,217

[22] Filed: Jan. 27, 1995

[51] Int. Cl.⁶ ..................................................... A61F 2/80
[52] U.S. Cl. ................................ 623/33; 623/36; 602/23; 602/62
[58] Field of Search ................................ 623/32, 33–34, 623/35, 36; 602/23, 60, 62, 63–72

[56] References Cited

U.S. PATENT DOCUMENTS

| | | | |
|---|---|---|---|
| 3,945,046 | 3/1976 | Stromgren | 602/63 |
| 4,139,002 | 2/1979 | Almedia | 602/26 |
| 4,842,608 | 6/1989 | Marx et al. . | |
| 4,872,879 | 10/1989 | Shamp | 623/36 |
| 4,981,132 | 1/1991 | Chong | 602/23 |
| 4,988,360 | 1/1991 | Shamp . | |
| 5,108,455 | 4/1992 | Telikicherla . | |
| 5,211,667 | 5/1993 | Danforth . | |
| 5,301,370 | 4/1994 | Henson | 602/60 |
| 5,385,534 | 1/1995 | Cassford | 602/23 |

FOREIGN PATENT DOCUMENTS 2512666  3/1983  France ...................................... 623/32

OTHER PUBLICATIONS

Wilson, Improvement of the Air–Cushion Socket for Below–Knee Amputees, Ottawa 1984.

Primary Examiner—John G. Weiss
Assistant Examiner—Bruce E. Snow
Attorney, Agent, or Firm—Harris Beach & Wilcox

[57] ABSTRACT

A post operative adjustable protective socket for a patient that has undergone a transtibial amputation. The socket is formed of a single piece of semi-rigid plastic and includes a cup shaped base, a semi-circular rear shell and a semi-circular front shell that are vertically extended from the base. The rear shell has two opposed circumferential cuffs that surround the wearer's leg above the knee. The front shell extends upwardly to a height just below the cuffs. Wide elastic bands surround the upper and lower sections of the device to press the shells into secure contact against the residual limb. A support strap also surrounds the device in the region of the wearer's patella tendon to help absorb some of the impact in the event of a fall.

12 Claims, 4 Drawing Sheets

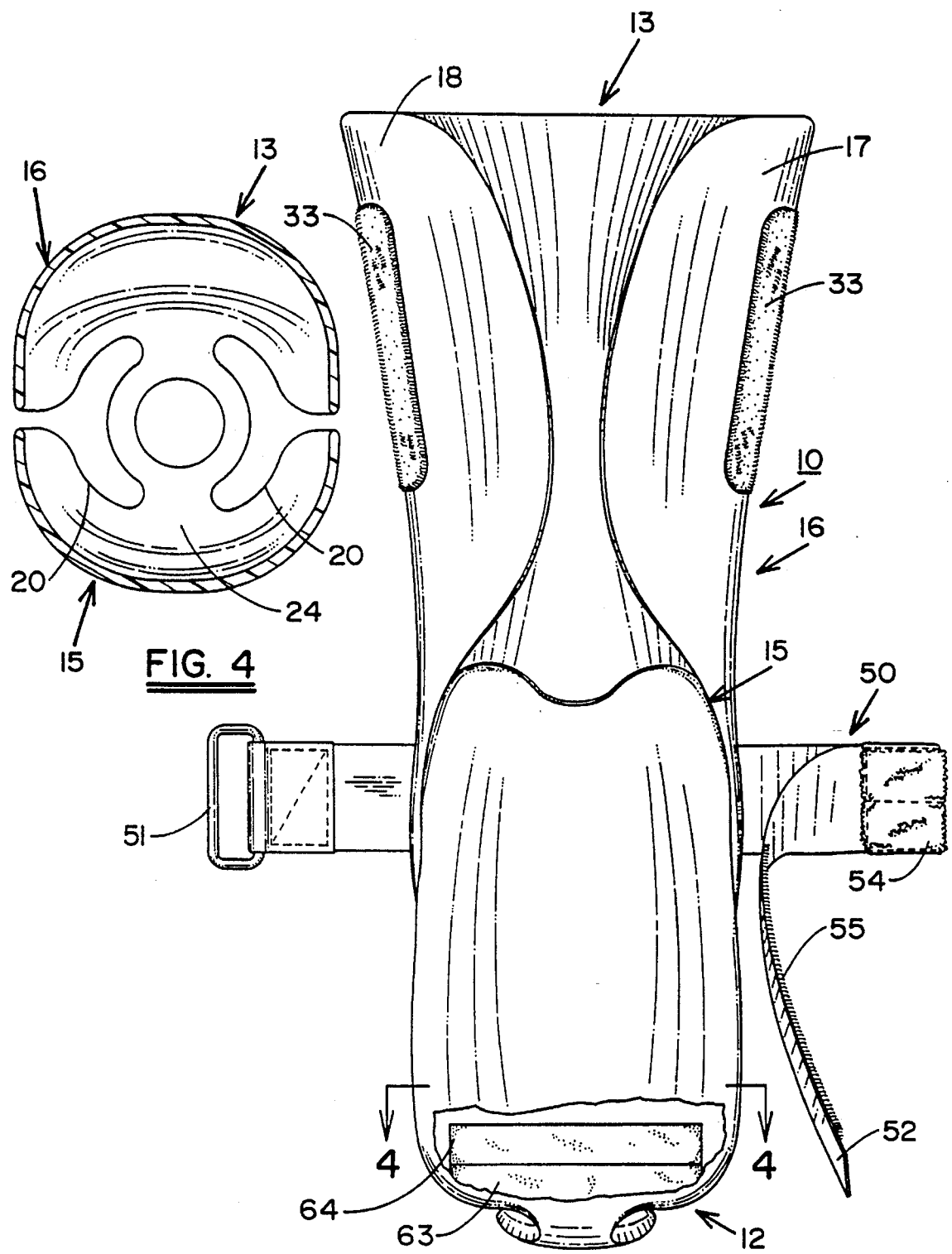

POST-OPERATIVE PROTECTIVE PROSTHESIS

BACKGROUND OF THE INVENTION

This invention relates to an adjustable post-operative prosthetic socket and, in particular, to a post operative protective socket that can be worn over a bandage and dressing while still providing easy access to the wound.

In U.S. Pat. No. 4,842,608 to Marx, there is described a protective prosthetic socket for post operative use by a transtibial (below the knee) amputee. As noted in the Marx patent, persons who have lost a lower limb can be fitted immediately after surgery with a prosthetic socket to protect the wound during the early stages of rehabilitation. Such amputees are subject to falling because of their initial inability to cope with one limb or simply because the patient forgot that he or she has lost part of a limb and attempts to place weight on the residual limb. These falls can be, at times, dangerous and damaging to the wound and thus extends the rehabilitation period.

After surgery, there is considerable swelling in and about the wound area. The wound is generally dressed and wrapped with a compressive bandage to reduce the swelling. Most post operative protective devices, although custom fitted, will not maintain pressure contact with the residual limb as the swelling subsides and thus fail to provide the restraint. More importantly, these custom fitted devices do not provide easy or ready access to the wound area when the wound or the bandage needs attention.

The Marx patent addresses some, but not all of the problems associated with post operative protective sockets. The Marx device involves three separate parts that are cojoined in assembly using a number of tensioning devices that include a screw jack, a ratchet mechanism and straps adapted to encircle the various component parts of the device. The three pieces are adapted to provide adjustability between parts to accommodate for variations in the residual limb size as the swelling is gradually reduced during the healing process. The Marx socket is rather complex in design and is therefore difficult to properly fit and accurately mount on the residual limb without assistance. The interrelated parts, through usage, can shift out of position in relation to each other and the device therefore will be unable to restrict knee flexion contractures to the degree required during post operative recovery. The Marx device, because of its many mechanical components, does not provide easy access to the wound area, nor does it prepare and shape the residual limb for a more permanent prosthetic device.

Danforth, in U.S. Pat. No. 5,211,667 describes a prosthesis for protecting a residual limb after a lower limb amputation. The device involves an upper shell that is specifically contoured to the patient's residual limb and a lower shell that is telescoped tightly into the upper shell. A stump sock having a flexible strip hanging from its distal end is required to be worn by the user. The flexible strip is passed through a series of holes formed in the sections and is ultimately fastened to the exterior surface of the lower shell to hold the parts in assembly. In the event of a fall, the lower shell is forced upwardly into the upper shell to cushion the impact of the fall. However, this telescoping action can, under certain circumstances, compress the upper shell around the wound area and thus, in the case of a fall producing high impact loading, may actually cause harm rather than prevent it.

SUMMARY OF THE INVENTION

It is therefore an object of the present invention to improve post operative protective prosthetic sockets used by a transtibial amputee.

It is a further object of the present invention to provide a post operative protective socket that is fully adjustable and provides ready and easy access to the wound area.

A still further object of the present invention is to help buildup a transtibial amputee patient's tolerance for a permanent prosthetic socket by use of a protective socket that shapes and prepares the residual limb for the more permanent device.

Another object of the present invention is to provide a post operative protective socket that restricts knee flexion contractions, while at the same time maintaining correct extension and alignment of the residual limb.

Yet another object of the present invention is to provide a one piece post operative protective socket that allows for measured and controlled weight bearing in the event of a fall.

These and other objects of the present invention are attained by means of a post operative prosthesis deice for protecting the residual limb of a wearer who has undergone a transtibial amputation. The device is formed of a single piece of semi-rigid plastic and includes a cup shaped base, a first semi-circular rear shell and a second semi-circular front shell, both of which extend upwardly from the base to form a semi-rigid sleeve for the residual limb. The top section of the rear shell has circumferential cuffs that are arranged to surround the residual limb above the knee. The front shell extends vertically to a height just below the cuffs. Wide elastic bands surround the upper and lower sections of the sleeve and serve to compress the sleeve inwardly against the limb. An adjustable strap is also secured to the rear shell and is passed around the top part of the front shell at about the level of the wearer's patella tendon. The strap is positioned to impart the shock of impact to the lower part of the knee rather than to the wound area.

BRIEF DESCRIPTION OF THE DRAWINGS

For a better understanding of these and other objects of the present invention, reference will be made to the following detailed description of the invention which is to be read in conjunction with the accompanying drawings, wherein:

FIG. 3 is a front view of the prosthesis device shown in FIG. 2;

FIG. 4 is a spatial sectional view taken along lines 4—4 in FIG. 3; and

DESCRIPTION OF THE INVENTION

Figure 1:
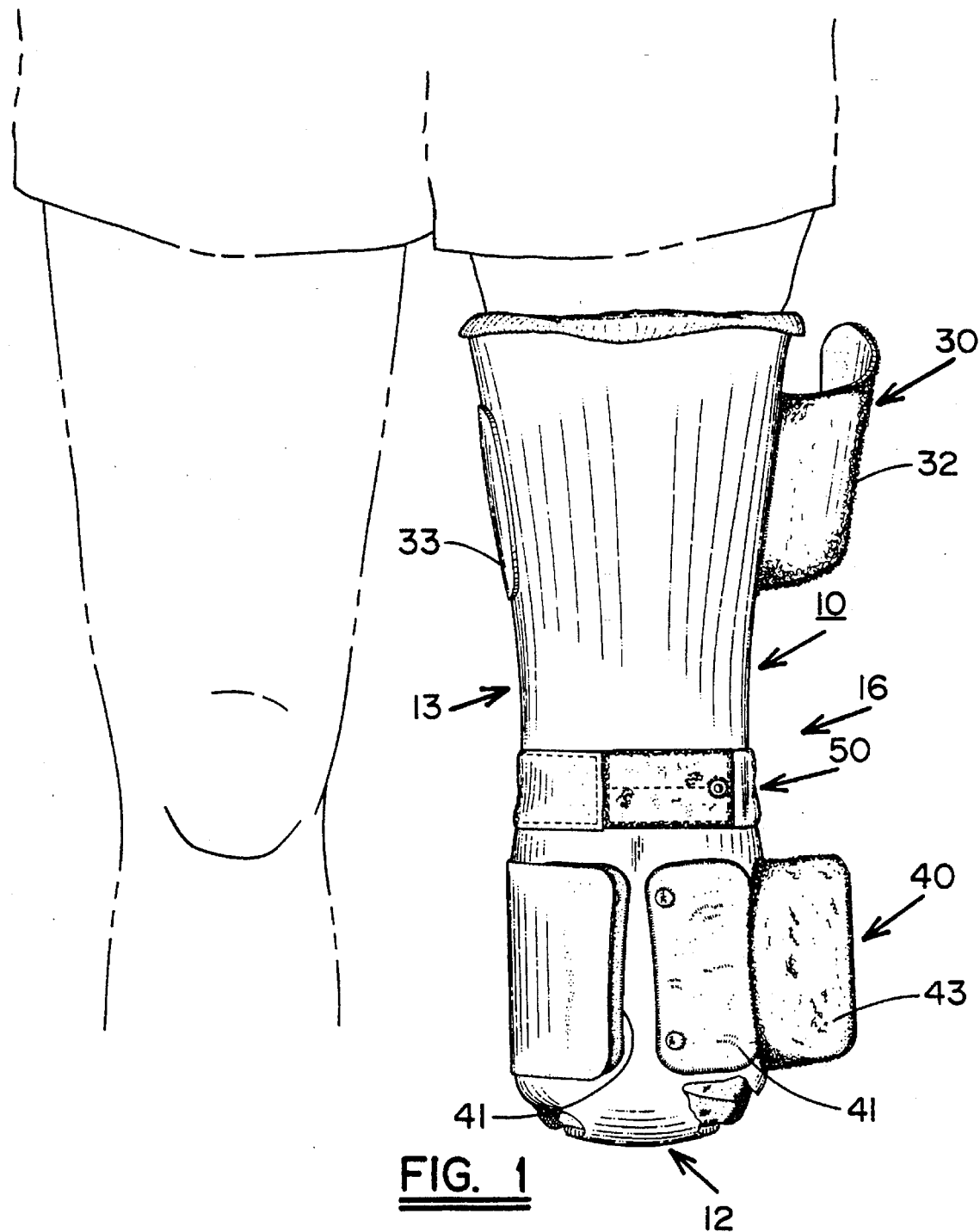
FIG. 1 is a rear view showing the prosthesis device of the present invention being worn on the residual limb of an amputee who has recently undergone a transtibial amputation.

Referring now to the drawings, there is illustrated a post operative protective prosthetic socket generally referenced 10 that embodies the teachings of the present invention. The device is designed to replace awkward and uncomfortable plaster or fiberglass casts that have heretofore been used to protect the wound area of an amputation site. As will become evident from the disclosure below, this post operative device enhances healing, permits the rehabilitation process to begin early on, and provides protection against possible wound deprivation due to a potentially damaging stumble or fall.

The present prosthetic socket is made of light-weight semi-rigid plastic, preferably polyethylene, that is molded into a single piece structure that can be easily removed and reapplied to the residual limb of a patient that recently underwent a transtibial amputation. The device provides ready access to the amputation site so that both the wound and the bandages surrounding the wound can be attended to when such attention is required. The device can be easily adjusted to accommodate elastic wraps or shrinkers that are typically applied to the wound area to reduce swelling.

During the critical period of rehabilitation, the present system will resist knee flexion contractures while at the same time maintaining proper knee alignment. As the healing process progresses, the semi-rigid adjustable device also helps shape and prepare the residual limb for a permanent prosthesis. It also allows for controlled and measurable weight bearing thus enabling the patient to gradually build the tolerance needed to support a permanent prosthesis.

The present post operative protective socket 10 includes a cup shaped base 12 at its distal end. A pair of semi-circular shaped elongated shells which are integral with the base, extend upwardly from the base section. These shells include a rear shell 13 and a front shell 15. The rear shell is brought to a higher elevation so that it passes over the wearer's knee and covers a portion of the wearer's thigh above the knee. The upper part of the rear shell further includes a pair of opposed cuffs 17 and 18 that are arranged to wrap circumferentially around the thigh.

The front shell, in turn, is brought to height so that it passes upwardly beyond the level of the wearer's patella tendon. The front shell substantially fills the region under the cuffs so that the two shells cooperate to form a semi-rigid outer protective sleeve 16 that can be easily passed over the residual limb and adjusted to accommodate bandages and the like, as well as maintaining a proper fit as swelling is reduced.

The lower section of the front shell is provided with a pair of edge slots or grooves 20—20 at the point where it joins the base section thereby reducing the joint area between the base and the shell. This reduced section 24 of plastic serves as a living hinge that allows the front and rear shells to be compressed inwardly to reduce the overall circumference of the lower section of the socket. By the same token, the two opposed cuffs located at the top section of the rear shell can be compressed to again reduce the circumference in the upper part of the sleeve.

A wide elastic band 30 (FIG. 1) is wrapped around the cuffs and is secured at both ends to the outer wall of the rear shell by means of Velcro fasteners. A loop strip 32 is sewn into the back of the band which can be attached to loop pads 33—33 secured by any suitable means to the rear shell. As can be seen, the band can be drawn tightly around the cuffs to compress the top section of the sleeve and thus adjustably tighten the cuff about the upper part of the patient's limb.

A second wide elastic band 40 is similarly wrapped about the lower part of the sleeve. Here again, a pair of hook pads 41—41 are secured to the rear face of the rear sleeve. The band has a loop strip 43 sewn into its back surface. The band, in assembly, is attached to one of the pads and is looped around behind the front shell before being attached to the second pad. The belt can be selectively tightened around the sleeve to draw the front shell inwardly and thus compress the lower section of the sleeve about the wearer's limb below the knee.

An adjustable strap 50 is also secured as by rivets to the rear face of the rear sleeve in the area of the patient's patella tendon. One end of the strap contains a buckle 51 through which the other free end of the strap 52 can be threaded. A loop pad 54 is sewn into the top face of the strap adjacent to the front sleeve. A cooperating loop pad 55 is similarly sewn into the top face of the strap adjacent to the free end 52 of the strap. In assembly, the free end of the strap is passed around the back of the front shell, through the buckle and the pads are brought together to close the loop.

Figure 2:
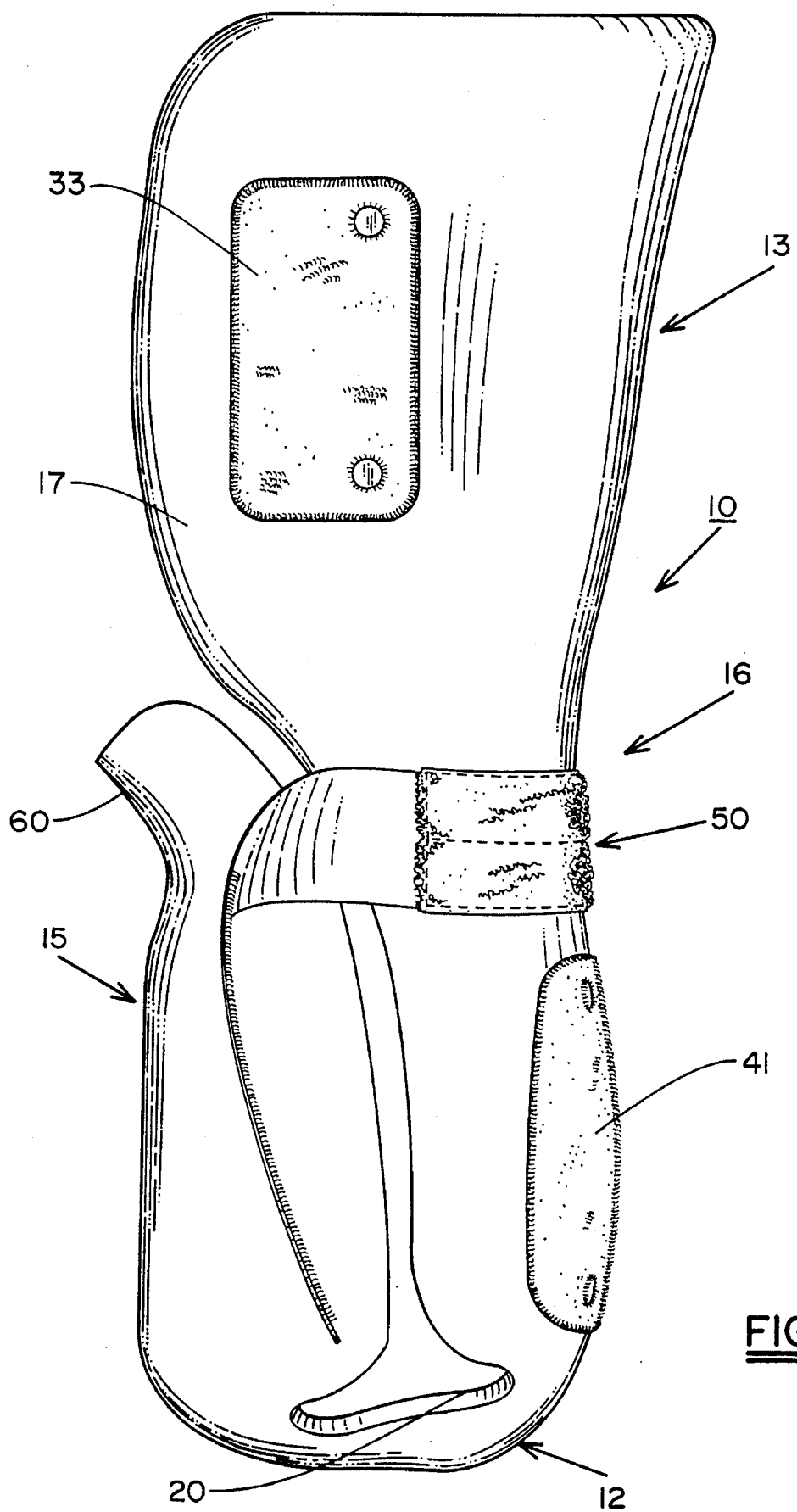
FIG. 2 is an enlarged side elevation of the prosthesis device shown in FIG. 1.
Figure 5:
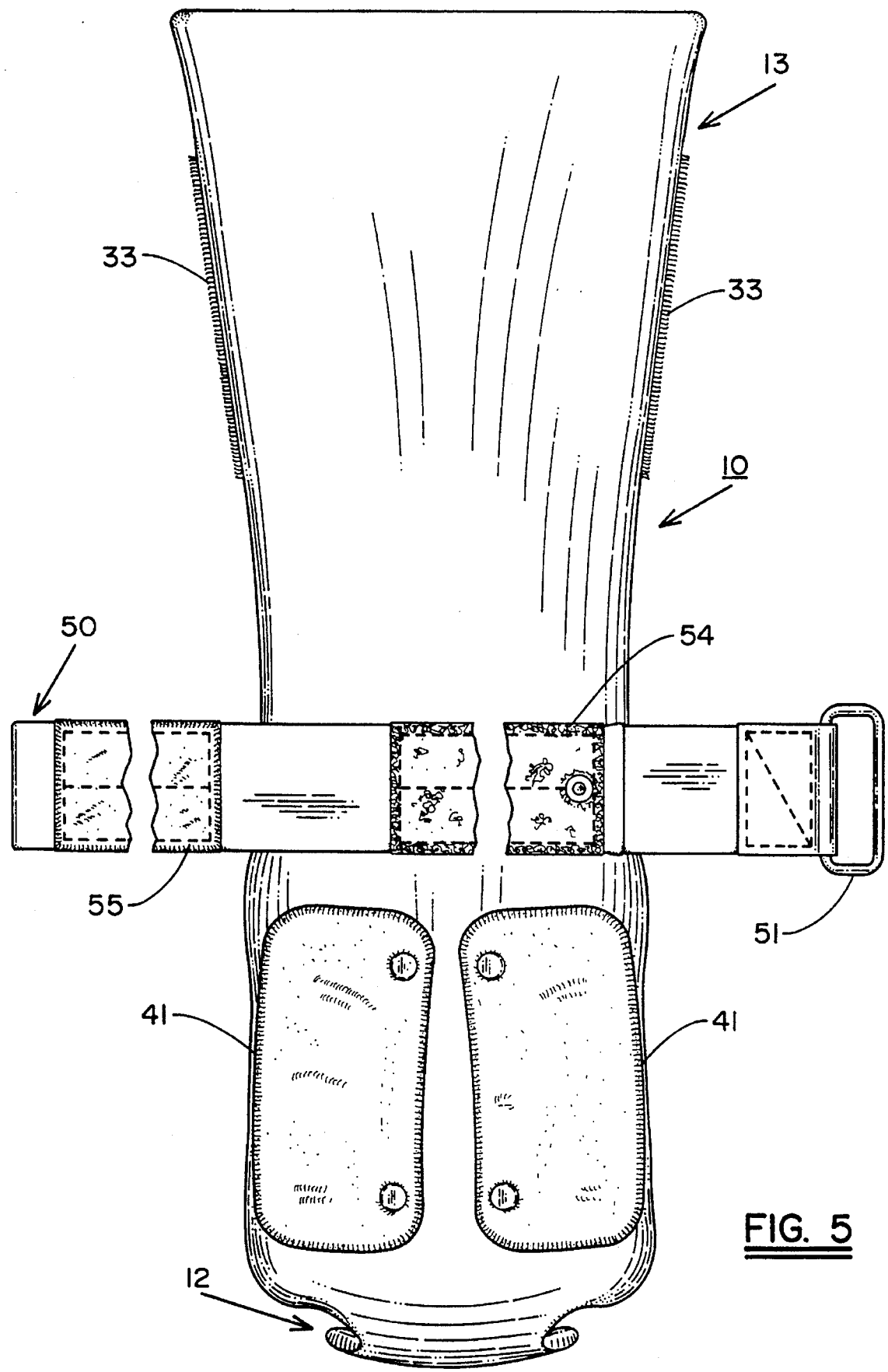
FIG. 5 is a rear view of the prosthesis device shown in FIG. 3.

The upper section of the front shell is provided with an outwardly protruding lip 60 (FIG. 2) that serves to both position the strap in relation to the front shell and locate the strap at about the level of the wearer's patella tendon. This allows the strap to be tightened just below the knee to again draw the front shell inwardly and furnish additional protection in the event of a potentially dangerous fall. The strap, in conjunction with the plastic socket, will absorb a good deal, if not most, of the force of an impact in the event of a fall and transmit this force to the limb in the knee region where it will produce little harm.

A pair of resilient pads 63 and 64 (FIG. 3) are placed one upon the other in the cup of the base. The lower pad (63) may be secured to the base by an adhesive while the upper pad 64 is cut to a measured width to receive the distal end of the residual limb thus further protecting the limb in the event of a fall.

While this invention has been explained with reference to the structure disclosed herein, it is not confined to the details set forth and this invention is intended to cover any modifications and changes as may come within the scope of the following claims:

What is claimed is:

1. A post operative prosthesis device for protecting the residual limb of a wearer after a transtibial amputation that includes a prosthetic device formed of a semi-rigid plastic, said device having a circular cup-shaped base, a semi-circular cross-section elongated rear shell and a semi-circular cross-section front shell, both of which extend vertically upwardly from said base such that said base, from shell and rear shell are integrally molded into a single piece of plastic to form a sleeve receiving a residual limb therein, said rear shell having a pair of opposed cuffs that extend circumferentially from the upper part thereof adapted to encompass the wearer's limb above the knee, said front shell extending vertically to a height just below the circumferential cuffs of said rear shell, elastic means for encircling the sleeve and compressing the shells inwardly toward the wearer's limb, and an adjustable strap secured to the rear shell that surrounds the top of the front shell adapted to be positioned at about the level of the wearer's patella tendon whereby the strap can be tightened about the shells to provide additional protection against impact forces in the event of a fall.

2. The prosthetic device of claim 1 that further includes resilient pad means mounted within said base.

3. The prosthetic device of claim 2 wherein said resilient means includes a bottom pad affixed to the inside surface of said base and a removable top pad seated upon the bottom pad.

4. The prosthetic device of claim 1 wherein said front shell has a top edge that is turned outwardly to form a lip which prevents the strap from moving over the top of said front shell.

5. The prosthetic device of claim 1 wherein said band means is adjustably secured to one of the shells by means of hook and loop pads.

6. The prosthetic device of claim 1 that further includes a pair of circumferential slots formed between the base and the front shell to permit the front shell to be compressed inwardly.

7. The prosthetic device of claim 1 wherein the base and the two shells are formed of a single piece of polyethylene.

8. A post operative prosthesis device for protecting the residual limb of a wearer after a transtibial amputation that includes a prosthetic device formed of a semi-rigid plastic, said device having a circular cup-shaped base, a semi-circular cross-section elongated rear shell and a semi-circular cross-section front shell, both of which extend vertically upwardly from said base to form a sleeve for receiving a residual limb therein, said rear shell having a pair of opposed cuffs that extend circumferentially from the upper part of the rear shell adapted to encompass the wearer's limb above the knee, said front shell extending vertically to a height just below the circumferential cuffs of said rear shell, a first elastic band adjustably secured to the upper part of the rear shell adapted to be positioned above the wearer's knee, and surrounding the opposed cuffs whereby said cuffs are adjustably closed about the wearer's limb above the knee;

second elastic band adapted to be adjustably secured to the lower part of the rear shell adapted to be positioned below the wearer's knee, said second elastic band surrounding the front shell whereby said front shell is adapted to be adjustably closed against the back of the wearers limb below the knee, and, an adjustable strap secured to one of the shells that surround the top of the front shell adapted to be positioned at about the level of the wearers patella tendon whereby the strap can be tightened about the shells to provide support below the knee.

9. The prosthetic device of claim 8 wherein said second band has a vertical width substantially equal to the vertical distance between the top of the base and the bottom of said strap.

10. The prosthetic device of claim 8 wherein said bands are adjustably secured to the rear shell by means of hook and loop pads.

11. The prosthetic device of claim 8 that further includes a pair of circumferential slots formed between the base and the front shell to allow the shell to be compressed inwardly.

12. The prosthetic device of claim 8 wherein the base and the two shells are formed of a single piece of polyethylene.

* * * * *

UNITED STATES PATENT AND TRADEMARK OFFICE
CERTIFICATE OF CORRECTION

PATENT NO. : 5,571,209

DATED : November 5, 1996

INVENTOR(S) : Robert N. Brown, Sr.

It is certified that error appears in the above-indentified patent and that said Letters Patent is hereby corrected as shown below:

Column 4, line 41, "from" should read --front--.

Column 4, line 42, "sleeve receiving" should read --sleeve for receiving--.

Signed and Sealed this

Sixth Day of May, 1997

Attest:

Attesting Officer

BRUCE LEHMAN

Commissioner of Patents and Trademarks